United States Patent
Ujhazy et al.

(12) 
(10) Patent No.: US 7,697,990 B2
(45) Date of Patent: Apr. 13, 2010

(54) METHOD AND APPARATUS FOR DETECTION AND TREATMENT OF RESPIRATORY DISORDER BY IMPLANTABLE DEVICE

(75) Inventors: Anthony John Ujhazy, East Lindfield (AU); Gregory Newton Brewer, Croydon (AU)

(73) Assignee: Resmed Limited, NSW (AU)

( * ) Notice: Subject to any disclaimer, the term of this patent is extended or adjusted under 35 U.S.C. 154(b) by 70 days.

(21) Appl. No.: 10/598,136

(22) PCT Filed: Feb. 21, 2005

(86) PCT No.: PCT/AU2005/000225

§ 371 (c)(1),
(2), (4) Date: Aug. 18, 2006

(87) PCT Pub. No.: WO2005/079909

PCT Pub. Date: Sep. 1, 2005

(65) Prior Publication Data

US 2007/0150022 A1 Jun. 28, 2007

Related U.S. Application Data

(60) Provisional application No. 60/546,551, filed on Feb. 20, 2004.

(51) Int. Cl.
*A61N 1/08* (2006.01)
(52) U.S. Cl. ...................................... 607/42
(58) Field of Classification Search .......... 128/204.23, 128/848, 204.18; 600/9, 407, 534, 537, 547, 600/593, 529; 607/17, 20, 42; 623/1.15
See application file for complete search history.

(56) References Cited

U.S. PATENT DOCUMENTS

| 4,830,008 A | | 5/1989 | Meer | |
|---|---|---|---|---|
| 5,158,080 A | * | 10/1992 | Kallok | 607/42 |
| 5,178,156 A | * | 1/1993 | Takishima et al. | 600/537 |
| 5,207,230 A | * | 5/1993 | Bowers | 600/593 |
| 5,540,733 A | * | 7/1996 | Testerman et al. | 607/42 |

(Continued)

FOREIGN PATENT DOCUMENTS

EP 0507580 7/1996

(Continued)

OTHER PUBLICATIONS

Tompsett, Ralph. "Cheyne-Stokes Respiration." Encyclopedia Americana. 2008. Grolier Online. Jan. 4, 2008 <http://ea.grolier.com/cgi-bin/article?assetid=0090330-00>.*

(Continued)

*Primary Examiner*—Carl H Layno
*Assistant Examiner*—Luther G Behringer
(74) *Attorney, Agent, or Firm*—Gottlieb Rackman & Reisman, PC

(57) ABSTRACT

Methods and apparatus for detection and treatment of respiratory disorders using implanted devices are described. In one form, afferent nerves are electrically or electro-mechanically stimulated to increase the tone of upper airway muscles. Detection of respiratory disorders is carried out using electrodes implanted in sub-pectoral regions. Open and closed airway apneas are distinguished using a combination of acoustic detectors and electrical transducers.

19 Claims, 1 Drawing Sheet

U.S. PATENT DOCUMENTS

Figure 1:
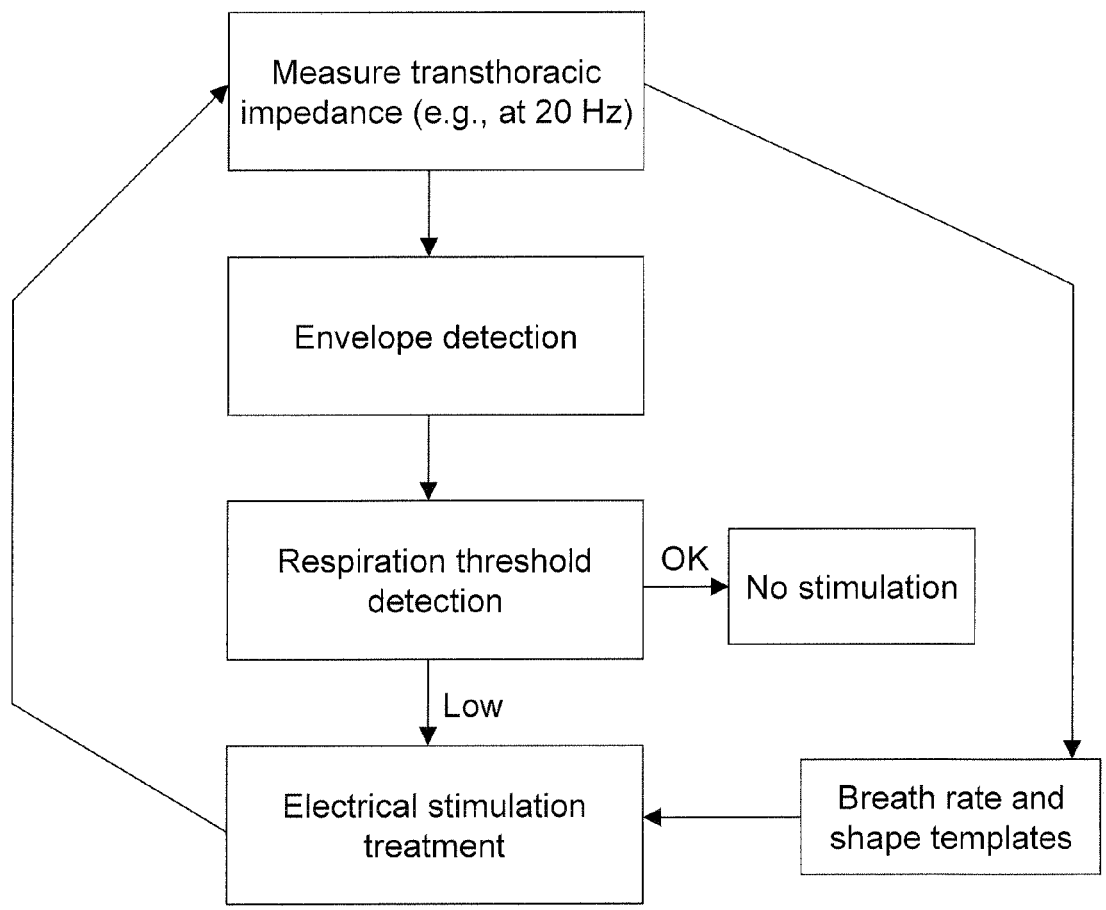

| | | | |
|---|---|---|---|
| 6,076,015 A * | 6/2000 | Hartley et al. | 607/20 |
| 6,240,316 B1 * | 5/2001 | Richmond et al. | 607/42 |
| 6,251,126 B1 * | 6/2001 | Ottenhoff et al. | 607/42 |
| 6,904,320 B2 * | 6/2005 | Park et al. | 607/17 |
| 2002/0049479 A1 * | 4/2002 | Pitts | 607/42 |
| 2004/0002742 A1 * | 1/2004 | Florio | 607/19 |
| 2004/0102712 A1 * | 5/2004 | Belalcazar et al. | 600/547 |
| 2004/0111040 A1 * | 6/2004 | Ni et al. | 600/534 |
| 2004/0186526 A1 * | 9/2004 | Freeberg | 607/17 |
| 2005/0004610 A1 * | 1/2005 | Kim et al. | 607/17 |
| 2005/0039745 A1 * | 2/2005 | Stahmann et al. | 128/204.18 |
| 2005/0043644 A1 * | 2/2005 | Stahmann et al. | 600/529 |

FOREIGN PATENT DOCUMENTS

| | | |
|---|---|---|
| EP | 0702977 | 3/2003 |
| WO | 9215364 | 9/1992 |
| WO | 9221407 | 12/1992 |

OTHER PUBLICATIONS

Hill, Richard W. "Respiration." Encyclopedia Americana. 2008. Grolier Online. Jan. 4, 2008 <http://ea.grolier.com/cgi-bin/article?assetid=0331290-00>.*

Merriam-Webster Online Dictionary Jan. 4, 2008 <http://m-w.com/dictionary/afferent>.*

* cited by examiner

METHOD AND APPARATUS FOR DETECTION AND TREATMENT OF RESPIRATORY DISORDER BY IMPLANTABLE DEVICE

The present application claims priority to U.S. Provisional patent application 60/546,551 filed 20 Feb. 2004.

1.0 FIELD OF THE INVENTION

The invention relates to the detection and treatment of respiratory disorders by implantable electrical and/or electromechanical devices.

2.0 BACKGROUND

Nasal CPAP treatment of Sleep Disordered Breathing (SDB), for example as taught by Sullivan in U.S. Pat. No. 4,944,310 has become the standard. However, other techniques are known. Uvulopalatopharyngoplasty (UPPP) is a surgical procedure for the treatment of severe Obstructive Sleep Apnea (OSA). In UPPP, soft tissue on the back of the throat and soft palate (the uvula) is removed. Oral Mandibular Advancement Devices are dental appliances used to treat patients with Obstructive Sleep Apnea (OSA) and Upper Airway Resistance Syndrome (UARS). They look similar to mouth guards used in sports. Other techniques involve electrical stimulation.

U.S. Pat. No. 6,636,767 describes how an electrode is placed in stimulating contact with an airway passage-controlling muscle of the patient. The electrode is energized to contract the muscle and alter the airway passage.

However some researchers have noted (Guilleminault et al. Chest 1995 107:67-73) that "The results obtained by us and others do not, at this time, give convincing support for the use of electrical stimulation using submental surface or intraoral electrodes as a viable approach for effective control of obstructive sleep apnea syndrome symptoms."

It is known that central apnea and obstructive apnea can be discriminated by flow and effort sensors. See for example U.S. Pat. Nos. 6,675,797; 6,029,665; and 6,445,942.

It is an object of the invention to provide improved detection and treatment of respiratory disorders using implanted devices.

3.0 SUMMARY OF THE INVENTION

In accordance with a first aspect of the invention, treatment of a respiratory disorder utilises afferent nerve stimulation.

In accordance with a second aspect of the invention, treatment of a respiratory disorder utilises efferent nerve stimulation.

In accordance with another aspect of the invention, upper airway muscle tone is indirectly stimulated.

In accordance with another aspect of the invention, baseline treatment is initiated when the patient is asleep in order to achieve an increased background tone of upper airway muscles to prevent airway collapse.

In accordance with another aspect of the invention, treatment is initiated or increased above baseline treatment when obstructive sleep apnea is detected.

In accordance with another aspect of the invention, respiratory disorders are detected with the use of an implanted device.

In accordance with another aspect of the invention, open and closed airway (also called, central and obstructive) apneic events are distinguished by a combination of implanted electrodes and acoustic transducers.

4.0 BRIEF DESCRIPTION OF THE DRAWING

FIG. 1 shows a method for detection and treatment of respiratory disorders using implantable devices.

5.0 DETAILED DESCRIPTION OF PREFERRED EMBODIMENTS

5.1 Treatment

For treatment of detected Obstructive Sleep Apnea (OSA), one method is electrical stimulation of afferent nerves, the objective of which is to indirectly cause an increase of the tone of upper airway muscles normally involved with maintenance of upper airway patency. In OSA, it is known that tone of these upper airway muscles typically decreases, contributing to a collapse and obstruction of the airway. Typically during wakefulness in patients with OSA, reflexes work to maintain tone in upper airway muscles thereby preventing airway collapse. The object of the present method is to substitute or enhance this reflex mechanism during sleep, thereby restoring or maintaining airway patency. The site of electrical stimulation is within or adjacent to the genioglossus muscle or in the vicinity of the hypoglossal motor nucleus or excitatory afferent nerve pathways leading to this structure. The amplitude, frequency and pulse width of electrical stimulation is controlled such that sufficient stimulation of afferent nerves is achieved without significant stimulation of efferent nerves, and without eliciting arousal from sleep. This stimulation of afferent nerves thus influences the patient's own intrinsic control system which modulates upper airway tone. The electrical simulation of afferent nerves typically consists of trains of electrical pulses, for example; 0.1 mA amplitude, 0.1 ms duration, train length of 10-30 pulses repeated every 1 minute. This level is defined as 1 unit of stimulation.

A second method for stimulation of afferent nerves is by using mechanical stimulation. A mechanical element, for example a piezo-electric element, is implanted at a site in the vicinity of the upper airway, for example, within or adjacent to the base of the genioglossus muscle. The element is electrically connected to the controller of the implanted device. The controller elicits vibration of the mechanical element by sending an electrical signal. Vibration of the element elicits stimulation of mechanoreceptor afferent nerve endings within the upper airway. Stimulation of these mechanoreceptors provides an excitatory input into the patient's intrinsic control system of the upper airway, thereby increasing tone of upper airway muscles and hence restoring or maintaining airway patency. The amplitude, frequency and duration of the mechanical stimulation are controlled such that sufficient stimulation of afferent nerves is achieved without sensory stimulation sufficient to cause arousal from sleep. The mechanical stimulation of afferent nerves would typically be achieved by a period of several seconds of vibration at frequencies in the range of 10-50 Hz, and is tuned to the frequency at which the target receptors are most sensitive. The repetition rate of the stimulation is controlled according to the detected state of the airway.

For either electrical or mechanical stimulation, the level of stimulation depends on 2 factors: 1) sleep state; 2) state of upper airway. When the patient is awake, no treatment is delivered. When the patient is asleep, a baseline treatment is delivered which has the objective of increasing the background tone of the upper airway muscles such that it is similar to the tone during the awake state. This is designed to pre-emptively reduce the incidence of airway collapse. When the patient is asleep and airway obstruction is detected, treatment above the level of the baseline treatment is delivered which has the objective of restoring airway patency. Sleep state is determined by a combination of time of day and postural state, for example when the patient is supine and the time of day is coincident with the patient's normal sleeping time, sleep state is determined as asleep. Time of day is determined by a real time clock within the implanted device and postural state by a position sensor, also contained within the implanted device. When the sleep state is asleep, the baseline level of treatment is initiated. When the sleep state is asleep and obstruction is detected, the level of treatment is increased and maintained until such time as airway obstruction is no longer detected, as follows:

| Sleep State/Airway State | awake | asleep | Asleep plus airway obstruction |
|---|---|---|---|
| Treatment level | No treatment | Baseline treatment of 0-5 units | Incremental above baseline of 1-10 units |

An example of a methodology as described is illustrated in FIG. 1.

5.2 Detection of Respiratory Disorders Via Implanted Electrodes

5.2.1 Impedance

Implanted electrodes are ideally placed one either side of the thoracic cavity. e.g. one electrode is placed in the left sub pectoral region and a second electrode in the right sub pectoral region. One of these electrodes could be incorporated into the metallic case of an implanted device.

The transthoracic impedance is measured by emitting high frequency (e.g. 20 Hz) electrical pulses (compared with respiration or heart rate) that have amplitude and duration below the level needed to stimulate excitable tissue.

Typically current pulses of 1 mA amplitude and 15 micro second duration are emitted at a 20 Hz. This level of energy is well below the level required to stimulate excitable tissue.

The impedance changes are calculated by measuring current & voltage and calculating impedance via Ohm's Law. Impedance changes are correlated with thorax movements. Patterns of movement are detected and used to indicate a variety of respiratory disorders such as Obstructive Apnea, central apnea, Cheyne-Stokes respiration (CS-R).

To detect impedance changes the instantaneous transthoracic impedance signal is compared to a baseline reference. e.g. the baseline reference is a continuously updated average of the most recent 30 minutes of the transthoracic impedance signal.

The changes to the transthoracic impedance signal are analysed in order to determine the state of respiration as follows:

| Respiration type | Transthoracic impedance |
|---|---|
| Normal respiration - no SDB | rhythmic variations at a rate of between 6 and 25 per minute; this rate averaged over; eg 2 minutes. Similarily an amplitude reference for 'normal breathing' is also derived; eg average amplitude of rhythmic variations over 30 minutes. |
| Obstructive | Marked reduction of amplitude as compared to the above reference; eg reduction of 30% or more; for at least 10 seconds. |
| Central apnea | first derivative of the impedance signal = essentially zero; no rhythmic variations for a period of 10 seconds or more |
| CSR | Derive the envelope of the rhythmic variations. Crescendo-decrescendo pattern denoted by a rhythmic variation in the envelope with a period of typically between 40 and 120 seconds or other classifier system. |

5.2.2 Impedance and Acoustic Transducers

A method for measuring airflow in an implantable device is by use of an acoustic transducer inside the device, such as a microphone, or from a transmitted signal from an external device in communication with the implantable device. Analysis of the frequency and amplitude of the sound can be used to deduce relative airflow. In addition, snoring, which is indicative of a partial obstruction of the upper airway can be detected. It is known that snoring is frequently a precursor of obstructive apnea.

A method for indicating thoracic movement is by measuring the electrical impedance between two or more implanted electrodes.

By a combination of methods for deducing airflow and thoracic movement, it is possible to discriminate between central and obstructive apnea in an implantable device. For example, if thoracic movements are detected without corresponding airflow, it is possible to deduce that there is obstructive apnea occurring. If there is no airflow and no thoracic movements for a specified period, it is possible to deduce that there is central apnea.

The invention claimed is:

1. A method of treating sleep disordered breathing comprising the steps of:
   implanting a device in a patient,
   determining the likelihood of said patient being asleep,
   delivering treatment so as to prevent airway collapse if said patient is likely to be asleep,
   determining the presence of an obstruction in said patient's airway, and
   if an obstruction is present increasing said treatment until said obstruction is no longer present,
   wherein said device includes a stimulator for providing electrical stimulation to afferent nerves, a postural sensor to sense said patient's postural state, a real time clock, and a detector to detect transthoracic impedance changes by 1) emitting high frequency electrical pulses to traverse the transthoracic cavity, 2) calculating instantaneous transthoracic impedance across said transthoracic cavity, and 3) comparing said instantaneous transthoracic impedance to a recent average of instantaneous transthoracic impedances,
   said treatment comprises operating said stimulator to apply electrical stimulation to afferent nerves,
   said presence of an obstruction is determined by detecting a change in transthoracic impedance, and the likelihood of said patient being asleep is determined based upon the time of day as identified by said real time clock together with the patient's postural state as sensed by said postural sensor.

2. The method of claim 1 wherein the site of electrical stimulation is within or adjacent to the genioglossus muscle.

3. The method of claim 1 wherein the site of electrical stimulation is in the vicinity of the hypoglossal motor nucleus or excitatory afferent nerve pathways leading to this structure.

4. The method of claim 1 wherein the electrical stimulation comprises trains of electrical pulses.

5. The method of claim 4 wherein the train length is approximately 10-30 pulses.

6. The method of claim 1 wherein stimulation is repeated in accordance with the detected state of the airway.

7. The method of claim 1 wherein stimulation is carried out in accordance with a model of Cheyne-Stokes Respiration.

8. A method of treating sleep disordered breathing comprising the steps of:
   implanting a device in a patient,
   determining the likelihood of said patient being asleep,
   delivering treatment so as to prevent airway collapse if said patient is likely to be asleep,
   determining the presence of an obstruction in said patient's airway, and
   if an obstruction is present increasing said treatment until said obstruction is no longer present,
   wherein said device includes a stimulator for providing mechanical stimulation to afferent nerves, a postural sensor to sense said patient's postural state, a real time clock, and a detector to detect transthoracic impedance changes by 1) emitting high frequency electrical pulses to traverse the transthoracic cavity, 2) calculating instantaneous transthoracic impedance across said tranathoracic cavity, and 3) comparing said instantaneous transthoracic impedance to a recent average of instantaneous transthoracic impedances,
   said treatment comprises operating said stimulator to apply mechanical stimulation to afferent nerves,
   said presence of an obstruction is determined by detecting a change in transthoracic impedance, and
   the likelihood of said patient being asleep is determined based upon the time of day as identified by said real time clock together with the patient's postural state as sensed by said postural sensor.

9. The method of claim 8 wherein mechanical stimulation is performed by a piezo-electric mechanical element implanted at a site in the vicinity of the patients upper airway.

10. The method of claim 9 wherein the piezo-electric mechanical element is implanted within or adjacent to the base of the genioglossus muscle.

11. The method of claim 8 wherein the mechanical stimulation is periodic.

12. The method of claim 11 wherein the duration of stimulation is on the order of several seconds of vibration.

13. The method of claim 8 wherein the mechanical vibration occurs at frequencies in the range of 10-50 Hz.

14. The method of claim 8 wherein stimulation is repeated in accordance with a detected change in transthoracic impedance.

15. The method of claim 8 wherein stimulation is carried out in accordance with a model of Cheyne-Stokes Respiration.

16. An apparatus for treating respiratory disorders in a patient adapted for implant within or adjacent to the base of genioglossus muscle, comprising:
   a piezo-electric mechanical element;
   a detector to detect transthoracic impedance changes;
   a controller adapted to elicit vibration of the piezo-electric mechanical element via an electrical signal to prevent airway collapse during sleep, to determine the presence of an obstruction, and to adjust said vibration upon the presence of an obstruction;
   a real time clock for determining time of day; and
   a postural sensor for sensing postural state;
   wherein said piezo-electric mechanical element is vibrated only for combinations of time of day and postural state that indicate that said patient is likely to be asleep and if an obstruction is present increasing said treatment until said obstruction is no longer present,
   the likelihood of said patient being asleep is determined based upon the time of day as identified by said real time clock together with the patient's postural state as sensed by said postural sensor,
   said detector detects transthoracic impedance changes by 1) emitting high frequency electrical pulses to traverse the transthoracic cavity, 2) calculating instantaneous transthoracic impedance across said transthoracic cavity, and 3) comparing said instantaneous transthoracic impedance to a recent average of instantaneous transthoracic impedances; and
   said controller determines the presence of an obstruction is determined based upon a detected change in transthoracic impedance.

17. An apparatus for treating respiratory disorders in a patient adapted for implant within or adjacent to the base of genioglossus muscle, comprising:
   a stimulator for providing electrical stimulation to a patient's afferent nerves;
   a detector to detect transthoracic impedance changes;
   a controller adapted to elicit electrical stimulation of said stimulator to prevent airway collapse during sleep, to determine the presence of an obstruction, and if an obstruction is present increasing said treatment until said obstruction is no longer present;
   a real time clock for determining time of day; and
   a postural sensor for detecting postural state
   wherein said stimulator provides stimulation only for combinations of time of day and postural state that indicate that said patient is likely to be asleep,
   the likelihood of said patient being asleep is determined based upon the time of day as identified by said real time clock together with the patient's postural state as sensed by said postural sensor,
   said detector detects transthoracic impedance changes by 1) emitting high frequency electrical pulses to traverse the transthoracic cavity, 2) calculating instantaneous transthoracic impedance across said transthoracic cavity, and 3) comparing said instantaneous transthoracic impedance to a recent average of instantaneous transthoracic impedances, and
   said controller determines the presence of an obstruction based upon said detector detecting a change in transthoracic impedance.

18. An apparatus for treating respiratory disorders in a patient adapted for implant within or adjacent to the base of genioglossus muscle, comprising:
   a stimulator for providing stimulation to a patient's afferent nerves;
   a detector to detect transthoracic impedance changes; and a controller adapted to 1) determine whether said patient is likely to be asleep, 2) elicit stimulation from said stimulator upon determining that said patient is asleep to prevent airway collapse during sleep, 3) determining the presence of an obstruction, and 4) adjusting said stimulation upon the presence of an obstruction;

wherein said detector detects transthoracic impedance changes by 1) emitting high frequency electrical pulses to traverse the transthoracic cavity, 2) calculating instantaneous transthoracic impedance signal across said transthoracic cavity, and 3) comparing said instantaneous transthoracic impedance to a recent average of instantaneous transthoracic impedances, and said controller determines the presence of an obstruction based upon said detector detecting changes in transthoracic impedance.

19. An apparatus for treating respiratory disorders in a patient adapted for implant within or adjacent to the base of genioglossus muscle, comprising:

a stimulator for providing electrical stimulation to a patient's afferent nerves;

a detector to detect transthoracic impedance changes;

a controller adapted to elicit electrical stimulation of said stimulator to prevent airway collapse during sleep, to determine the presence of an obstruction, and if an obstruction is present increasing said treatment until said obstruction is no longer present;

a real time clock for determining time of day; and wherein said stimulator provides stimulation for selected times of day when said patient is likely to be asleep, the likelihood of said patient being asleep is determined based upon the time of day as identified by said real time clock, said detector detects transthoracic impedance changes by 1) emitting high frequency electrical pulses to traverse the transthoracic cavity, 2) calculating instantaneous transthoracic impedance transthoracic impedance across said transthoracic cavity, and 3) comparing said instantaneous signal to a recent average of instantaneous transthoracic impedances, and said controller determines the presence of an obstruction based upon said detector detecting changes in transthoracic impedance.

* * * * *